United States Patent
Rapoport

(10) Patent No.: US 9,864,029 B2
(45) Date of Patent: Jan. 9, 2018

(54) MEANS FOR OPERATING AN MRI DEVICE WITHIN A RF-MAGNETIC ENVIRONMENT

(71) Applicant: Aspect Imaging Ltd., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 458 days.

(21) Appl. No.: 14/596,320

(22) Filed: Jan. 14, 2015

(65) Prior Publication Data
US 2015/0212172 A1    Jul. 30, 2015

Related U.S. Application Data

(60) Provisional application No. 61/932,820, filed on Jan. 29, 2014.

(51) Int. Cl.
| | |
|---|---|
| *G01R 33/422* | (2006.01) |
| *G01R 33/34* | (2006.01) |
| *H01P 11/00* | (2006.01) |
| *A61B 5/055* | (2006.01) |

(52) U.S. Cl.
CPC .......... *G01R 33/422* (2013.01); *A61B 5/055* (2013.01); *G01R 33/34* (2013.01); *H01P 11/007* (2013.01); *A61B 2562/182* (2013.01); *Y10T 29/49016* (2015.01); *Y10T 29/49018* (2015.01)

(58) Field of Classification Search
CPC ..... G01R 33/422; G01R 33/34; H01P 11/007; Y10T 29/49016; Y10T 29/49018; A61B 2562/182
See application file for complete search history.

(56) References Cited

U.S. PATENT DOCUMENTS

| | | | |
|---|---|---|---|
| 5,159,929 A * | 11/1992 | Morris ................ | A61B 5/055 174/351 |
| 8,851,018 B2 | 10/2014 | Rapoport et al. | |
| 8,896,310 B2 | 11/2014 | Rapoport | |
| 2003/0058502 A1* | 3/2003 | Griffiths ............... | G01R 33/283 398/139 |
| 2003/0088175 A1* | 5/2003 | Branch ................ | G01R 33/422 600/410 |
| 2007/0135704 A1* | 6/2007 | Branch ................ | G01R 33/422 600/410 |

(Continued)

OTHER PUBLICATIONS

Aspect Imaging LTD., "Method for Previding High Resolution, High Contrast Fused MRI Images", co-pending U.S. Appl. No. 13/877,553, filed Apr. 3, 2013, 2015/0077105 A1 date Mar. 19, 2017.

(Continued)

*Primary Examiner* — Rodney Bonnette
(74) *Attorney, Agent, or Firm* — Pearl Cohen Zedek Latzer Baratz LLP

(57) ABSTRACT

An MRI device that reduces radio-frequency (RF) interference and the effect of the MRI's magnet, within an active RF-magnetic environment. The device relies on a shield. The device includes a uniform non-fringing magnetic field resonance device (UNF-MRD), an RF shielding means either embedded within or in connection with the UNF-MRD for providing the UNF-MRD a radio interference immunity (RII) from RF-electromagnetic environment surrounding the same.

29 Claims, 5 Drawing Sheets

(56) References Cited

U.S. PATENT DOCUMENTS

| | | | |
|---|---|---|---|
| 2010/0000780 A1* | 1/2010 | Zhu | H01B 11/1895 174/350 |
| 2011/0162652 A1 | 3/2011 | Rapoport | |
| 2011/0186049 A1 | 3/2011 | Rapoport | |
| 2011/0234347 A1 | 9/2011 | Rapoport | |
| 2011/0304333 A1 | 12/2011 | Rapoport | |
| 2012/0071745 A1 | 3/2012 | Rapoport | |
| 2012/0073511 A1 | 3/2012 | Rapoport et al. | |
| 2012/0077707 A1 | 3/2012 | Rapoport | |
| 2012/0118630 A1* | 5/2012 | Jiang | G01R 33/36 174/74 R |
| 2012/0119742 A1 | 5/2012 | Rapoport | |
| 2013/0079624 A1 | 3/2013 | Rapoport | |
| 2013/0109956 A1 | 5/2013 | Rapoport | |
| 2013/0237803 A1 | 5/2013 | Rapoport | |
| 2013/0328559 A1 | 12/2013 | Rapoport | |
| 2013/0328560 A1 | 12/2013 | Rapoport | |
| 2013/0328563 A1 | 12/2013 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0099010 A1 | 4/2014 | Rapoport | |
| 2014/0103927 A1 | 4/2014 | Rapoport | |
| 2014/0117989 A1 | 5/2014 | Rapoport | |
| 2014/0128725 A1 | 5/2014 | Rapoport | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0230850 A1 | 8/2014 | Rapoport | |
| 2014/0257081 A1 | 9/2014 | Rapoport | |
| 2014/0266203 A1 | 9/2014 | Rapoport | |
| 2014/0300358 A1 | 10/2014 | Rapoport | |
| 2014/0354279 A1* | 12/2014 | Dumoulin | G01R 33/422 324/318 |
| 2014/0378821 A1 | 12/2014 | Rapoport et al. | |
| 2014/0378825 A1 | 12/2014 | Rapoport et al. | |
| 2015/0065788 A1 | 3/2015 | Rapoport | |
| 2015/0137812 A1* | 5/2015 | Rapoport | G01R 33/288 324/318 |
| 2015/0141799 A1* | 5/2015 | Rapoport | A61B 5/0555 600/410 |
| 2015/0168519 A1* | 6/2015 | Rapoport | A61B 5/055 324/318 |
| 2015/0212173 A1* | 7/2015 | Rapoport | A61B 5/055 324/318 |
| 2015/0253400 A1* | 9/2015 | Rapoport | G01R 33/3804 324/318 |
| 2015/0253401 A1* | 9/2015 | Rapoport | A61B 5/055 324/318 |

OTHER PUBLICATIONS

Aspect Imaging LTD., "Method for Manipulating the MRI's Protocol of Pulse Sequences", co-pending U.S. Appl. No. 14/070,965, filed Nov. 4, 2013, 9557397 B2 date Jan. 31, 2017.

Aspect Imaging LTD., "Shutting Assembly for Closing and Entrance of an MRI Device", co-pending U.S. Appl. No. 14/540,163, filed Nov. 13, 2014, Rapoport 2015/0137812 A1 date May 21, 2015.

Aspect Imaging LTD, "MRI-Incubator's Closure Assembly", co-pending U.S. Appl. No. 14/539,442, filed Nov. 12, 2014, Rapoport et al. 2015/0141799 A1 date May 21, 2015.

Aspect Imaging LTD., "Cage in an MRD with a Fastening/Attenuating System", co-pending U.S. Appl. No. 14/527,950, filed Oct. 30, 2014, Rapoport 2015/0059157 A1 date Mar. 5, 2015.

Rapoport, Uri, "RF Shielding Conduit in an MRI Closure Assembly", co-pending U.S. Appl. No. 14/574,785, filed Dec. 18, 2014, Rapoport 2015/0168519 A1 date Jun. 18, 2015.

Aspect Imaging LTD., "System and Method for Generating Invasively Hyperpolarized Images", co-pending U.S. Appl. No. 14/556,682, filed Dec. 1, 2014, Rapoport 2015/0084630 A1 date Mar. 26, 2015.

Aspect Imaging LTD., "System and Method for Generating Invasively Hyperpolarized Images", co-pending U.S. Appl. No. 14/556,654, filed Dec. 1, 2014, Rapoport 2015/0087051 A1 date Mar. 26, 2015.

Aspect Imaging LTD., "MRI with Magnet Assembly Adapted for Convenient Scanning of Laboratory Animals with Automated RF Tuning Unit", co-pending U.S. Appl. No. 14/581,266, filed Dec. 23, 2014, Rapoport et al. 2015/0112186 A1 date Apr. 23, 2015.

Aspect Imaging LTD., "Chamber for Housing Animals During Anaesthetic Procedures", co-pending U.S. Appl. No. 14/537,266, filed Nov. 10, 2014, Rapoport 2015/0059655 A1 date Mar. 5, 2015.

Aspect Imaging LTD., "RF Automated Tuning System USed in a Magnetic Resonance Device and Methods Thereof", co-pending U.S. Appl. No. 14/588,741, filed Jan. 2, 2012, Rapoport et al. 2015/0201862 A1 date Jul. 23, 2015.

Aspect Imaging LTD., "Means and Method for Operating an MRI Device Within a RF-Magnetic Environment", co-pending U.S. Appl. No. 14/596,329, filed Jan. 14, 2015, Rapoport 2015/0212173 A1 date Jul. 21, 2015.

Aspect Imaging LTD., "CT/MRI Integrated System for the Diagnosis of Acute Strokes and Methods Thereof", co-pending U.S. Appl. No. 14/598,517, filed Jan. 16, 2015, Rapoport 2015/0208994 A1 date Jul. 30, 2015.

Aspect Imaging LTD., "Mechanical Clutch for MRI", co-pending U.S. Appl. No. 14/611,379, filed Feb. 2, 2015, Rapoport 9568571 B2 date Feb. 14, 2017.

Hashemi, et al., "Crisscross Artifact, MRI: The Basics", 2004, Second Edition, Lippincott Williams & Wilkins, Philadelphia, PA.

Aspect Imaging LTD., "Foamed Patient Transport Incubator", co-pending U.S. Appl. No. 14/531,289, filed Nov. 3, 2014, Rapoport 2015/0126804 A1 date May 7, 2015.

Aspect Imaging LTD., "Incubator Deployable Multi-Functional Panel", co-pending U.S. Appl. No. 14/619,557, filed Feb. 11, 2015, Rapoport 2015/0231012 A1 date Aug. 20, 2015.

Aspect Imaging LTD., "MRI Thermo-Isolating Jacket", co-pending U.S. Appl. No. 14/623,039, filed Feb. 16, 2015, Rapoport 2015/0253400 A1 date Sep. 10, 2015.

Aspect Imaging LTD., "MRI RF Shielding Jacket", co-pending U.S. Appl. No. 14/623,051, filed Feb. 16, 2015, Rapoport 2015/0253401 A1 date Sep. 10, 2015.

Aspect Imaging LTD., "Capsule for a Pneumatic Sample Feedway", co-pending U.S. Appl. No. 14/626,391, filed Feb. 19, 2015, Rapoport et al. 2015/0160311 A1 date Jun. 11, 2015.

Aspect Imaging LTD., "Incubator's Canopy with Sensor Dependent Variably Transparent Walls and Methods for Dimming Lights Thereof", co-pending U.S. Appl. No. 14/453,909, filed Aug. 7, 2014, Rapoport 2015/0073204 A1 date Mar. 12, 2015.

Aspect Imaging LTD., "Temperature-Controlled Exchangeable NMR Probe Cassette and Methods Thereof", co-pending U.S. Appl. No. 14/504,890, filed Oct. 2, 2014, Rabinovitz et al. 2016/0077176 A1 date Mar. 17, 2016.

Aspect Imaging LTD., "NMR Extractable Probe Cassette Means and Methods Thereof", co-pending U.S. Appl. No. 14/504,907, filed Oct. 2, 2014, Rabinovitz et al. 2016/0077171 A1 date Mar. 17, 2016.

* cited by examiner

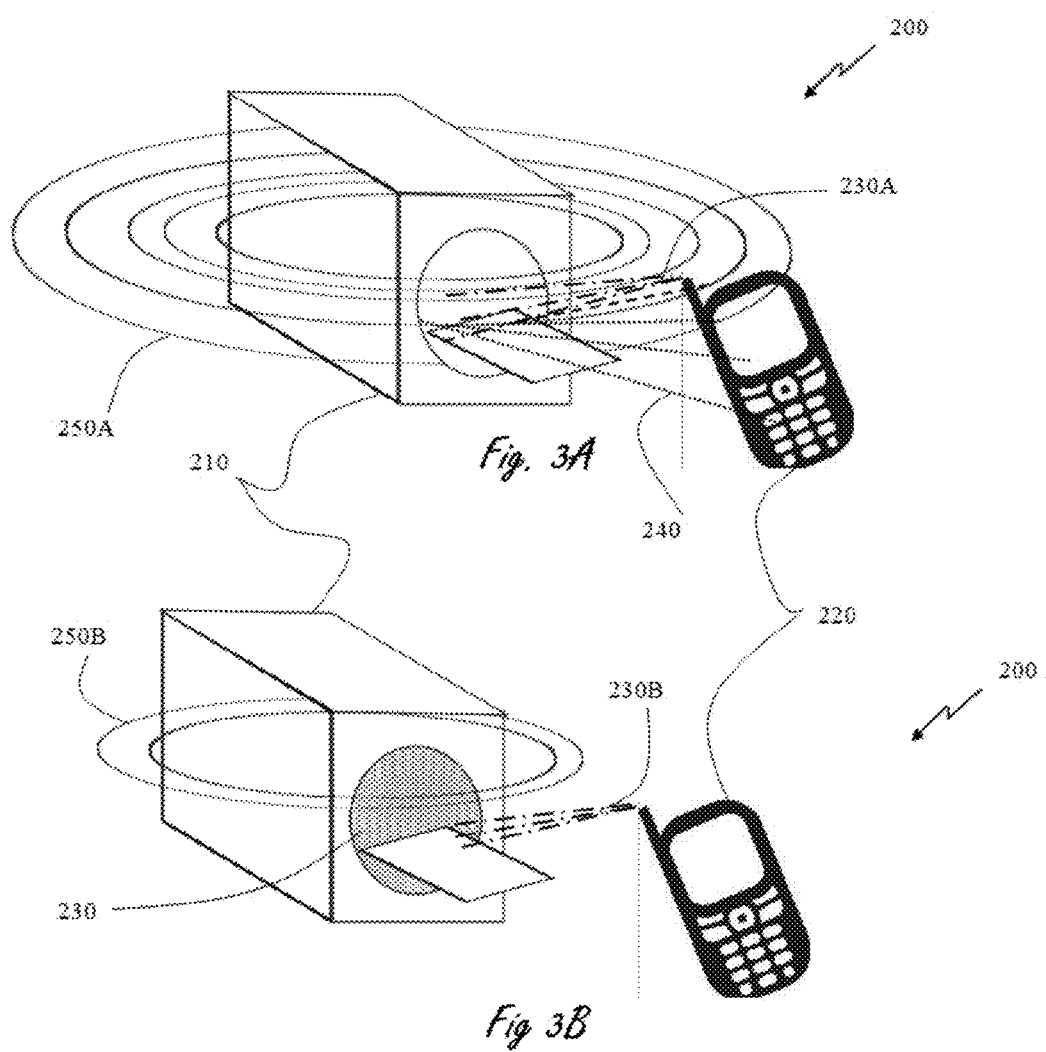

MEANS FOR OPERATING AN MRI DEVICE WITHIN A RF-MAGNETIC ENVIRONMENT

This patent application claims priority to U.S. Provisional Patent Application No. 61/932,820, filed Jan. 29, 2014, which is incorporated in its entirety by reference herein.

FIELD OF THE INVENTION

The present invention generally relates to an MRI device that reduces radio-frequency (RF) interference as well as reduces the effect of the MRI's magnet, within an active RF-magnetic environment. More particularly, the invention pertains to a non-fringing magnetic field resonance MRI device having RF shielding means, to methods thereof and to standard of care for safe operation of MRI devices in an RF-magnetic environment.

BACKGROUND OF THE INVENTION

Electromagnetic radiation (EMR) is a form of energy emitted and absorbed by charged particles which exhibit wave-like behavior as it travels through space. EMR is classified according to the frequency of its wave. It consists of radio waves, microwaves, infrared radiation, visible light, ultraviolet radiation, X-rays and gamma rays. The electromagnetic radiation is called radio-frequency (RF) radiation when it is within the radio wave range.

RF interference is disturbance that affects an electrical circuit due to either electromagnetic induction or electromagnetic radiation emitted from an external source within the radio wave range. The disturbance may interrupt, obstruct, or otherwise degrade or limit the effective performance of the circuit. These effects can range from a simple degradation of data to a total loss of data. The source may be any object, artificial or natural, that carries rapidly changing electrical currents, such as an electrical circuit, the Sun or the Northern Lights.

Hospital is an environment highly dense with apparatus emitting RF radiation, ranging from medical equipment, through communication devices such as intercoms and call units to electric personal gear of hospital staff, patients and their families. All these electric apparatus may interfere and disturb the function of each other.

The most important outcome of RF interference within a hospital is dysfunction of medical equipment. For example, an MRI that depends on an RF coil which its shift resulting from RF interference will change the readings of the machine and as a result will give inaccurate data. The RF interference will also obstruct RF-dependent cordless interaction between medical devices. For example, a monitor transmitting data to the nurse unit may send inaccurate and shifted signals that may cost a life. Although not life threatening, RF interference of medical devices with cellular reception is a burdensome nuisance, especially for patient and their relatives as well as the medical staff.

There thus remains a long felt and unmet need for a uniform non-fringing magnetic field resonance MRI device that functions within an active RF-magnetic environment without being affected by other ferromagnetic RF transmitting devices and without affecting their function.

SUMMARY OF THE INVENTION

According to one embodiment of the present invention, In a uniform non-fringing magnetic field resonance device (UNF-MRD), an RF shielding means for providing radio interference immunity (RII) to the UNF-MRD from RF-electromagnetic environment surrounding the same; wherein no RF and magnetic interference between the UNF-MRD and the RF-electromagnetic environment are generated.

According to another embodiment of the present invention, wherein the UNF-MRD comprising (a) a main longitudinal axis with a distal and proximal ends; (b) an open bore extended along the axis and terminated by an aperture located in the proximal end; and (c) a closure assembly which is shaped to fit the aperture.

According to another embodiment of the present invention, wherein the RF shielding means comprises an RF shielding conduit (RFSC), having apertures shaped to permit passage of medical equipment tubing from the external environment of the UNF-MRD to inner space of the bore, affixed to the closure assembly, the conduit is characterized by a length (l) and width (w), l:w ratio is greater than a predefined value n, thereby providing RF shielding.

According to another embodiment of the present invention, wherein the RFSC is connected in a non-protruding manner to the closure assembly, thereby indirect access is provided between the bore and the external environment.

According to another embodiment of the present invention, wherein the RFSC profile along the width is of a shape selected from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the present invention, wherein the RFSC comprises a wall along the length; the wall is of a shape selected from a group consisting of: straight, curved, polygonal, symmetrical, non-symmetrical and any combination thereof.

According to another embodiment of the present invention, wherein at least a portion of the RFSC comprises electromagnetic conductive material.

According to another embodiment of the present invention, wherein the conduit is configured to shield the passage of frequencies selected from a group consisting of: 0 to about 1000 MHz, 0 to about 500 MHz, 0 to about 200 MHz and any combination thereof.

According to another embodiment of the present invention, wherein the conduit is configured to shield electromagnetic interference by means selected from a group consisting of: waveguide, RF filter, waveguide filter, attenuating material, and any combination thereof.

According to another embodiment of the present invention, wherein at least a portion of the RFSC comprises shielding selected from a group consisting of: magnetic shielding, RF shielding, physical shielding and any combination thereof.

According to another embodiment of the present invention, wherein the RFSC is affixed to the closure assembly further comprising a hinge having at least one first connecting member connected to the UNF-MRD and at least one second connecting member, connected to the closure assembly, further wherein at least one first connecting member is maneuverably coupled to at least one second connecting member.

According to another embodiment of the present invention, wherein the RF shielding means comprises an RF shielding hinge (RFSH); the RFSH comprises at least one first connecting member connected to the UNF-MRD or the open bore thereof and at least one second connecting member, connected to the closure assembly; at least one first connecting member is maneuverably coupled to at least one second connecting member; the RFSH comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the present invention, wherein the RFSH member connected to the UNF-MRD is connected at a location selected from a group consisting of: at least a portion of the UNF-MRD external wall, within at least a portion of the bore, at least a portion of the UNF-MRD aperture perimeter and any combination thereof.

According to another embodiment of the present invention, wherein the hinge first connecting member is connected at a location, in respect to the UNF-MRD aperture, selected from a group consisting of: left, right, below, above and any combination thereof.

According to another embodiment of the present invention, wherein at least a portion of the RFSH comprises shielding selected from a group consisting of: magnetic shielding, RF shielding, physical shielding and any combination thereof.

According to another embodiment of the present invention, wherein the conduit is configured to shield the passage of frequencies selected from a group consisting of: 0-1000 MHz, 0-500 MHz, 0-200 MHz and any combination thereof.

According to another embodiment of the present invention, wherein the conduit is configured to shield electromagnetic interference by means selected from a group of: waveguide, RF filter, waveguide filter, attenuating material, and any combination thereof.

According to another embodiment of the present invention, wherein the RF interference is within a predetermined range.

According to another embodiment of the present invention, wherein the range is selected from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF shielding means reject frequencies in within a predetermined range.

The RF shielding means of claim 19, wherein the range is selected from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF-electromagnetic environment includes an item selected from a group consisting of RF welders, electronic article surveillance and RF identification devices, cordless phones, FM and AM broadcasting and receiving devices, and any combination thereof.

According to another embodiment of the present invention, wherein the RF interference is selected from a group consisting of continuous interference, transient interference, and any combination thereof.

According to another embodiment of the present invention, wherein the RII provided by the shielding is above a predetermined value.

According to another embodiment of the present invention, wherein the predetermined value is about 100 dB.

According to another embodiment of the present invention, wherein the magnetic field within a predetermined radius from the UNF-MRD is less than a predetermined value.

According to another embodiment of the present invention, wherein the predetermined radius is less than about 0.5 meter the predetermined value is less than about 20 mT.

20 mT is the weakest magnetism that may erase information from a credit card.

According to another embodiment of the present invention, wherein the RII provides no zipper effect in images produced by the UNF-MRD.

According to another embodiment of the present invention, wherein the UNF-MRD provides images with no Herringbone effect.

According to another embodiment of the present invention, wherein the UNF-MRD is compatible with ferromagnetic materials located further than a predetermined distance.

According to another embodiment of the present invention, wherein the predetermined distance is about 0.5 meters.

According to another embodiment of the present invention, a method for eliminating RF interference between a uniform non-fringing magnetic field resonance device (UNF-MRD) and an RF-electromagnetic environment surrounding the same, comprising steps of: (a) obtaining a UNF-MRD; and, (b) embedding RF shielding means; the RF shielding means provides radio interference immunity (RII) to the UNF-MRD from RF-electromagnetic environment; thereby, no RF and magnetic interference between the UNF-MRD and the RF-electromagnetic environment is generated.

According to another embodiment of the present invention, additionally comprising a step of providing the UNF-MRD with (a) a main longitudinal axis with a distal and proximal ends; (b) an open bore extended along the axis and terminated by an aperture located in the proximal end; and (c) a closure assembly which is shaped to fit the aperture.

According to another embodiment of the present invention, additionally comprising a step of selecting an RF shielding conduit (RFSC) for the RF shielding means, the RFSC having apertures shaped to permit passage of medical equipment tubing from the external environment of the UNF-MRD to inner space of the bore, affixed to the closure assembly, wherein the conduit is characterized by a length (l) and width (w), l:w ratio is greater than a predefined value n, thereby providing RF shielding.

According to another embodiment of the present invention, additionally comprising a step of connecting the RFSC in a non-protruding manner to the closure assembly, thereby providing indirect access between the bore and the external environment.

According to another embodiment of the present invention, additionally comprising a step of selecting the RFSC profile along the width is of a shape from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the present invention, additionally comprising a step of providing a wall along the length; the wall is of a shape selected from a group consisting of: straight, curved, polygonal, symmetrical, non-symmetrical and any combination thereof.

According to another embodiment of the present invention, additionally comprising a step of providing, to at least a portion of the RFSC, electromagnetic conductive material.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group consisting of: waveguide, RF filter, waveguide filter, attenuating material, and any combination thereof.

According to another embodiment of the present invention, additionally comprising a step of providing, to at least a portion of the RFSC, shielding selected from a group consisting of: magnetic shielding, RF shielding, physical shielding and any combination thereof.

According to another embodiment of the present invention, additionally comprising a step of affixing the RFSC to the closure assembly further comprising a hinge having at least one first connecting member connected to the UNF-MRD and at least one second connecting member, connected to the closure assembly, further wherein at least one first connecting member is maneuverably coupled to at least one second connecting member.

According to another embodiment of the present invention, additionally comprising a step of selecting an RF shielding hinge (RFSH) for the RF shielding means; the RFSH comprises at least one first connecting member connected to the UNF-MRD or the open bore thereof and at least one second connecting member, connected to the closure assembly; at least one first connecting member is maneuverably coupled to at least one second connecting member; the RFSH comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the present invention, additionally comprising a step of connecting the RFSH member to the UNF-MRD is connected at a location selected from a group consisting of: at least a portion of the UNF-MRD external wall, within at least a portion of the bore, at least a portion of the UNF-MRD aperture perimeter and any combination thereof.

According to another embodiment of the present invention, additionally comprising a step of connecting the hinge first connecting member at a location, in respect to the UNF-MRD aperture, selected from a group consisting of: left, right, below, above and any combination thereof.

According to another embodiment of the present invention, additionally comprising a step of selecting at least a portion of the RFSH comprises shielding from a group consisting of: magnetic shielding, RF shielding, physical shielding and any combination thereof.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group of: waveguide, RF filter, waveguide filter, attenuating material, and any combination thereof.

According to another embodiment of the present invention, additionally comprising a step of defining the RF interference within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, additionally comprising a step of rejecting the RF shielding means frequencies in within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF-electromagnetic environment includes an item selected from a group consisting of RF welders, electronic article surveillance and RF identification devices, cordless phones, FM and AM broadcasting and receiving devices, and any combination thereof.

According to another embodiment of the present invention, additionally comprising a step of selecting the RF interference from a group consisting of continuous interference, transient interference, and any combination thereof.

According to another embodiment of the present invention, wherein the RII provided by the shielding is above a predetermined value.

According to another embodiment of the present invention, wherein the predetermined value is about 100 dB.

According to another embodiment of the present invention, wherein the magnetic field within a predetermined radius from the UNF-MRD is less than a predetermined value.

According to another embodiment of the present invention, wherein the predetermined radius is less than about 0.5 meter the predetermined value is less than about 20 mT.

According to another embodiment of the present invention, additionally comprising a step of providing no zipper effect by the RII in images produced by the UNF-MRD.

According to another embodiment of the present invention, additionally comprising a step of providing by the UNF-MRD images with no Herringbone effect.

According to another embodiment of the present invention, wherein the UNF-MRD is compatible with ferromagnetic materials located further than a predetermined distance.

According to another embodiment of the present invention, wherein the predetermined distance is about 0.5 meters.

According to another embodiment of the present invention, wherein subjects going through an imaging process in the UNF-MRD are not obligated to be detached from medical equipment.

According to another embodiment of the present invention, additionally comprising a step of passing the medical equipment tubing through the conduit.

According to another embodiment of the present invention, a method for manufacturing a uniform non-fringing magnetic field resonance device (UNF-MRD) for imaging within an RF-electromagnetic environment surrounding the same, comprising steps of: (a) obtaining an UNF-MRD; and, (b) embedding RF shielding means; the RF shielding means provides radio interference immunity (RII) to the UNF- MRD from RF-electromagnetic environment; thereby, no RF and magnetic interference between the UNF-MRD and the RF-electromagnetic environment is generated.

According to another embodiment of the present invention, additionally comprising a step of providing the UNF-MRD with (a) a main longitudinal axis with a distal and proximal ends; (b) an open bore extended along the axis and terminated by an aperture located in the proximal end; and (c) a closure assembly which is shaped to fit the aperture.

According to another embodiment of the present invention, additionally comprising a step of selecting an RF shielding conduit (RFSC) for the RF shielding means, the RFSC having apertures shaped to permit passage of medical equipment tubing from the external environment of the UNF-MRD to inner space of the bore, affixed to the closure assembly, wherein the conduit is characterized by a length (l) and width (w), l:w ratio is greater than a predefined value n, thereby providing RF shielding.

According to another embodiment of the present invention, additionally comprising a step of connecting the RFSC in a non-protruding manner to the closure assembly, thereby providing indirect access between the bore and the external environment.

According to another embodiment of the present invention, additionally comprising a step of selecting the RFSC profile along the width is of a shape from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the present invention, additionally comprising a step of providing a wall along the length; the wall is of a shape selected from a group consisting of: straight, curved, polygonal, symmetrical, non symmetrical and any combination thereof.

According to another embodiment of the present invention, additionally comprising a step of providing, to at least a portion of the RFSC, electromagnetic conductive material.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group consisting of: waveguide, RF filter, waveguide filter, attenuating material, and any combination thereof.

According to another embodiment of the present invention, additionally comprising a step of providing, to at least a portion of the RFSC, shielding selected from a group consisting of magnetic shielding, RF shielding, physical shielding and any combination thereof.

According to another embodiment of the present invention, additionally comprising a step of affixing the RFSC to the closure assembly further comprising a hinge having at least one first connecting member connected to the UNF-MRD and at least one second connecting member, connected to the closure assembly, further wherein at least one first connecting member is maneuverably coupled to at least one second connecting member.

According to another embodiment of the present invention, additionally comprising a step of selecting an RF shielding hinge (RFSH) for the RF shielding means; the RFSH comprises at least one first connecting member connected to the UNF-MRD or the open bore thereof and at least one second connecting member, connected to the closure assembly; at least one first connecting member is maneuverably coupled to at least one second connecting member; the RFSH comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the present invention, additionally comprising a step of connecting the RFSH member to the UNF-MRD is connected at a location selected from a group consisting of: at least a portion of the UNF-MRD external wall, within at least a portion of the bore, at least a portion of the UNF-MRD aperture perimeter and any combination thereof.

According to another embodiment of the present invention, additionally comprising a step of connecting the hinge first connecting member at a location, in respect to the UNF-MRD aperture, selected from a group consisting of: left, right, below, above and any combination thereof.

According to another embodiment of the present invention, additionally comprising a step of selecting at least a portion of the RFSH comprises shielding from a group consisting of: magnetic shielding, RF shielding, physical shielding and any combination thereof.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group of: waveguide, RF filter, waveguide filter, attenuating material, and any combination thereof.

According to another embodiment of the present invention, additionally comprising a step of defining the RF interference within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, additionally comprising a step of rejecting the RF shielding means frequencies in within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF-electromagnetic environment includes an item selected from a group consisting of RF welders, electronic article surveillance and RF identification devices, cordless phones, FM and AM broadcasting and receiving devices, and any combination thereof.

According to another embodiment of the present invention, additionally comprising a step of selecting the RF interference from a group consisting of continuous interference, transient interference, and any combination thereof.

According to another embodiment of the present invention, wherein the RII provided by the shielding is above a predetermined value.

According to another embodiment of the present invention, wherein the predetermined value is about 100 dB.

According to another embodiment of the present invention, wherein the magnetic field within a predetermined radius from the UNF-MRD is less than a predetermined value.

According to another embodiment of the present invention, wherein the predetermined radius is less than about 0.5 meter the predetermined value is less than about 20 mT.

According to another embodiment of the present invention, additionally comprising a step of providing no Zipper effect by the RII in images produced by the UNF-MRD.

According to another embodiment of the present invention, additionally comprising a step of providing by the UNF-MRD images with no Herringbone effect.

According to another embodiment of the present invention, wherein the UNF-MRD is compatible with ferromagnetic materials located further than a predetermined distance.

According to another embodiment of the present invention, wherein the predetermined distance is about 0.5 meters.

According to another embodiment of the present invention, wherein subjects going through an imaging process in the UNF-MRD are not obligated to be detached from medical equipment.

According to another embodiment of the present invention, additionally comprising a step of passing the medical equipment tubing through the conduit.

According to another embodiment of the present invention, a standard of care (SOC) method for imaging a uniform non-fringing magnetic field resonance device (UNF-MRD) for imaging within an RF-electromagnetic environment surrounding the same, comprising steps of: (a) obtaining an UNF-MRD; and, (b) embedding RF shielding means; the RF shielding means provides radio interference immunity (RII) to the UNF-MRD from RF-electromagnetic environment; thereby, no RF and magnetic interference between the UNF-MRD and the RF-electromagnetic environment is generated.

According to another embodiment of the present invention, additionally comprising a step of providing the UNF-MRD with (a) a main longitudinal axis with a distal and proximal ends; (b) an open bore extended along the axis and terminated by an aperture located in the proximal end; and (c) a closure assembly which is shaped to fit the aperture.

According to another embodiment of the present invention, additionally comprising a step of selecting an RF shielding conduit (RFSC) for the RF shielding means, the RFSC having apertures shaped to permit passage of medical equipment tubing from the external environment of the UNF-MRD to inner space of the bore, affixed to the closure assembly, wherein the conduit is characterized by a length (l) and width (w), l:w ratio is greater than a predefined value n, thereby providing RF shielding.

According to another embodiment of the present invention, additionally comprising a step of connecting the RFSC in a non-protruding manner to the closure assembly, thereby providing indirect access between the bore and the external environment.

According to another embodiment of the present invention, additionally comprising a step of selecting the RFSC profile along the width is of a shape from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the present invention, additionally comprising a step of providing a wall along the length; the wall is of a shape selected from a group consisting of: straight, curved, polygonal, symmetrical, non-symmetrical and any combination thereof.

According to another embodiment of the present invention, additionally comprising a step of providing, to at least a portion of the RFSC, electromagnetic conductive material.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group consisting of waveguide, RF filter, waveguide filter, attenuating material, and any combination thereof.

According to another embodiment of the present invention, additionally comprising a step of providing, to at least a portion of the RFSC, shielding selected from a group consisting of: magnetic shielding, RF shielding, physical shielding and any combination thereof.

According to another embodiment of the present invention, additionally comprising a step of affixing the RFSC to the closure assembly further comprising a hinge having at least one first connecting member connected to the UNF-MRD and at least one second connecting member, connected to the closure assembly, further wherein at least one first connecting member is maneuverably coupled to at least one second connecting member.

According to another embodiment of the present invention, additionally comprising a step of selecting an RF shielding hinge (RFSH) for the RF shielding means; the RFSH comprises at least one first connecting member connected to the UNF-MRD or the open bore thereof and at least one second connecting member, connected to the closure assembly; at least one first connecting member is maneuverably coupled to at least one second connecting member; the RFSH comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the present invention, additionally comprising a step of connecting the RFSH member to the UNF-MRD is connected at a location selected from a group consisting of: at least a portion of the UNF-MRD external wall, within at least a portion of the bore, at least a portion of the UNF-MRD aperture perimeter and any combination thereof.

According to another embodiment of the present invention, additionally comprising a step of connecting the hinge first connecting member at a location, in respect to the UNF-MRD aperture, selected from a group consisting of: left, right, below, above and any combination thereof.

According to another embodiment of the present invention, additionally comprising a step of selecting at least a portion of the RFSH comprises shielding from a group consisting of: magnetic shielding, RF shielding, physical shielding and any combination thereof.

According to another embodiment of the present invention, additionally comprising a step of configuring the conduit to shield the passage of frequencies selected from a group consisting of 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group of: waveguide, RF filter, waveguide filter, attenuating material, and any combination thereof.

According to another embodiment of the present invention, additionally comprising a step of defining the RF interference within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, additionally comprising a step of rejecting the RF shielding means frequencies in within a predetermined range.

According to another embodiment of the present invention, additionally comprising a step of selecting the range from a group consisting of (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF-electromagnetic environment includes an item selected from a group consisting of RF welders, electronic article surveillance and RF identification devices, cordless phones, FM and AM broadcasting and receiving devices, and any combination thereof.

According to another embodiment of the present invention, additionally comprising a step of selecting the RF interference from a group consisting of continuous interference, transient interference, and any combination thereof.

According to another embodiment of the present invention, wherein the RII provided by the shielding is above a predetermined value.

According to another embodiment of the present invention, wherein the predetermined value is about 100 dB.

According to another embodiment of the present invention, wherein the magnetic field within a predetermined radius from the UNF-MRD is less than a predetermined value.

According to another embodiment of the present invention, wherein the predetermined radius is less than about 0.5 meter the predetermined value is less than about 20 mT.

According to another embodiment of the present invention, additionally comprising a step of providing no zipper effect by the RII in images produced by the UNF-MRD.

According to another embodiment of the present invention, additionally comprising a step of providing by the UNF-MRD images with no Herringbone effect.

According to another embodiment of the present invention, wherein the UNF-MRD is compatible with ferromagnetic materials located further than a predetermined distance.

According to another embodiment of the present invention, wherein the predetermined distance is about 0.5 meters.

According to another embodiment of the present invention, wherein subjects going through an imaging process in the UNF-MRD are not obligated to be detached from medical equipment.

According to another embodiment of the present invention, additionally comprising a step of passing the medical equipment tubing through the conduit.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not necessarily obscured. In the accompanying drawing:

FIG. 3A is an illustration of an MRI device with no shielding means and infringing magnet within an active RF environment (200);

FIG. 3B is an illustration of an MRI device with shielding means and an infringing magnet within an active RF environment (200);

DETAILED DESCRIPTION OF THE PREFERRED EMBODIMENTS

Figure 1:
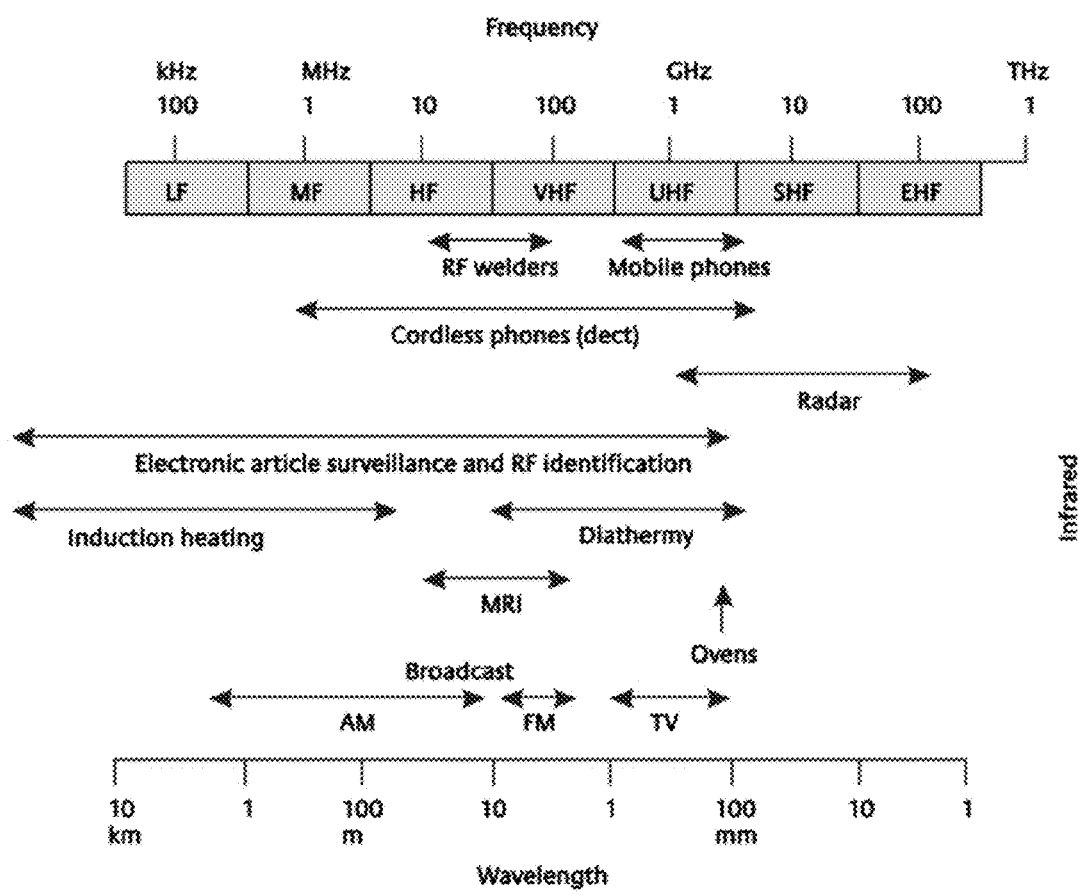
FIG. 1 schematically illustrates the RF spectrum and its sources.

The following description is provided, alongside all chapters of the present invention, so as to enable any person skilled in the art to make use of the invention and set forth the best modes contemplated by the inventor of carrying out this invention. Various modifications, however, will remain apparent to those skilled in the art, since the generic principles of the present invention is defined to specifically provide an MRI device have increased radio interference immunity (RII), decreased interfering effect on the RF environment and decreased magnetic attraction. The special features of the MRI device enable it to operate in an active RF-magnetic environment. The MRI device does not affect interfere with the RF environment as well as does not impose its magnetic affect. In addition, ferromagnetic items and RF transmitting electronic device does not interfere with the imaging properties of the MRI device.

An MRI device can affect and be affected on two levels: RF interference and magnetic field. It can cause RF interference to nearby electronic devices and be affected by them as well. The magnetism of the MRI can be affected by nearby ferromagnetic objects as well as its magnetic field may affect them.

The term "electromagnetic interference" interchangeably refers hereinafter to electromagnetic interference (EMI), and radio-frequency interference (RFI), derived from electromagnetic radiation, electromagnetic induction, magnetism, electrostatic fields etc., that affect any electrical circuit, or imaging device such as MRD, NMR, ESR, NQR, CT, US, etc. This interference is derived from any source natural or artificial such as earth magnetic field, atmospheric noise, moving masses of metal, electrical lines, subways, cellular communication equipment, electrical devices, TV and radio stations, elevators, etc. This interference can interrupt, obstruct, degrade, limit, result in false data, etc., the effective performance of the circuit or device.

The term "medical equipment" interchangeably refers hereinafter to all devices, tubes, connectors, wires, liquid carriers, needles, sensors, etc., that are used by medical staff in association with the patient. This medical equipment is used for various purposes such as life support, ventilating, temperature regulating, MRI contras solution injection, monitoring of cardio and breathing rates, viewing the patient, fluids transport, performing surgical operation, moving at least a part of the patient, etc.

The term "medical equipment tubing" interchangeably refers hereinafter to all tubes, cables, connectors, wires, liquid carriers, gas carriers, electrical wires, monitoring cables, viewing cables, data cables etc. that is used in connection to medical equipment or physical environment maintenance or monitoring.

The term "waveguide" interchangeably refers hereinafter to a structure that guides waves, such as electromagnetic waves or sound waves. The geometry of a waveguide reflects its function. Wave guides are constructed in different forms such as a hollow shape, solid rod, wire, etc. They are typically constructed from either conductive or dielectric materials. The frequency of the transmitted wave also dictates the shape of a waveguide. As depicted in Wikipedia, electromagnetic wave propagation along the axis of the waveguide is described by the wave equation, which is derived from Maxwell's equations, and where the wavelength depends upon the structure of the waveguide, and the material within it (air, plastic, vacuum, etc.), as well as on the frequency of the wave.

The term "RF filter" interchangeably refers hereinafter to components designed to filter signals in the MHz to GHz frequency ranges. This frequency range is the range used by most broadcast radio, television, wireless communication. These components exert some kind of filtering on the signals transmitted or received. The filters could be active or passive such as waffle-iron filter, mechanical RF filter, etc. RF filters are usually placed when there is need to pass an electrical wire in or out of an MRD enclosure to ensure that the EMI does not couple on the conductive wiring. These filters could be of passive components such as a combination of inductors and capacitors.

The term "hinge" interchangeably refers hereinafter to any connection in which one part is movable in respect to the other. The parts could be connected by a flexible mechanism or material, joint, hook, thread, axis, juncture, turning point, fold, bend, elbow, knee, corner, fork, axis, pole, pivot, ball and socket, condyloid joint, mechanical device, hinge, barrel hinge, pivot hinges, double-acting floor hinge, butt/mortise hinges, case hinges, continuous hinges, piano hinges, concealed hinges, cup hinge, euro hinge, butterfly hinges, parliament hinge, flag hinges, strap hinges, H hinges, HL hinges, counter-flap hinge, flush hinge, coach hinge, rising butt hinge, double action spring hinge, tee hinge, friction hinge, security hinge, cranked hinge, storm-proof hinge, lift-off hinge, self-closing hinge, butt hinge, etc.

The term "RF shielding" refers hereinafter to electromagnetic shielding that blocks radio frequency electromagnetic radiation.

The term "about" refers to a value being 20 percent greater or smaller than the defined measure.

The term "zipper effect" refers hereinafter to the effect caused by external interference resulting from external RF fields, as those caused by open doors, radios mobile telephones, electronic controls, etc. These emit interfering electromagnetic signals that hamper MRI image quality. Zipper effect appears as a region of increased noise with a width of 1 or 2 pixels that extends perpendicular to the frequency encoding direction, throughout the mage series. To date, in order to prevent this artifact, MRI devices are installed in RF free rooms (Faraday cages). Zipper artifact by Dr Jeremy Jones and Dr Usman Bashir et al. is incorporated here as a reference (See currently available internet link http://radiopaedia.org/articles/zipper-artifact).

The term "Herringbone artifact" refers hereinafter to an artifact appearing as a herringbone pattern scattered over the whole image in any direction on one slice or on multiple slices. The causes of this are many and various, e.g. electromagnetic spikes created by the gradients, electronic equipment inside the MR procedure room, or fluctuating AC current. Also known as Crisscross artifact. MRI: The Basics by Ray Hashman Hashemi, William G. Bradley, Christopher J. Lisanti, 2003, by Lippincott Williams & Wilkins, $2^{nd}$ Ed., is brought here as a reference.

According to one embodiment of the present invention, In a uniform non-fringing magnetic field resonance device (UNF-MRD), an RF shielding means for providing radio interference immunity (RII) to the UNF-MRD from RF-electromagnetic environment surrounding the same; wherein no RF and magnetic interference between the UNF-MRD and the RF-electromagnetic environment are generated.

According to another embodiment of the present invention, wherein the UNF-MRD comprising (a) a main longitudinal axis with a distal and proximal ends; (b) an open bore extended along the axis and terminated by an aperture located in the proximal end; and (c) a closure assembly which is shaped to fit the aperture.

According to another embodiment of the present invention, wherein the RF shielding means comprises an RF shielding conduit (RFSC), having apertures shaped to permit passage of medical equipment tubing from the external environment of the UNF-MRD to inner space of the bore, affixed to the closure assembly, the conduit is characterized by a length (l) and width (w), l:w ratio is greater than a predefined value n, thereby providing RF shielding.

According to another embodiment of the present invention, wherein the RFSC is connected in a non-protruding manner to the closure assembly, thereby indirect access is provided between the bore and the external environment.

According to another embodiment of the present invention, wherein the RFSC profile along the width is of a shape selected from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the present invention, wherein the RFSC comprises a wall along the length; the wall is of a shape selected from a group consisting of: straight, curved, polygonal, symmetrical, non symmetrical and any combination thereof.

According to another embodiment of the present invention, wherein at least a portion of the RFSC comprises electromagnetic conductive material.

According to another embodiment of the present invention, wherein the conduit is configured to shield the passage of frequencies selected from a group consisting of: 0 to about 1000 MHz, 0 to about 500 MHz, 0 to about 200 MHz and any combination thereof.

According to another embodiment of the present invention, wherein the conduit is configured to shield electromagnetic interference by means selected from a group consisting of: waveguide, RF filter, waveguide filter, attenuating material, and any combination thereof.

According to another embodiment of the present invention, wherein at least a portion of the RFSC comprises shielding selected from a group consisting of: magnetic shielding, RF shielding, physical shielding and any combination thereof.

According to another embodiment of the present invention, wherein the RFSC is affixed to the closure assembly further comprising a hinge having at least one first connecting member connected to the UNF-MRD and at least one second connecting member, connected to the closure assembly, further wherein at least one first connecting member is maneuverably coupled to at least one second connecting member.

According to another embodiment of the present invention, wherein the RF shielding means comprises an RF shielding hinge (RFSH); the RFSH comprises at least one first connecting member connected to the UNF-MRD or the open bore thereof and at least one second connecting member, connected to the closure assembly; at least one first connecting member is maneuverably coupled to at least one second connecting member; the RFSH comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the present invention, wherein the RFSH member connected to the UNF-MRD is connected at a location selected from a group consisting of: at least a portion of the UNF-MRD external wall, within at least a portion of the bore, at least a portion of the UNF-MRD aperture perimeter and any combination thereof.

According to another embodiment of the present invention, wherein the hinge first connecting member is connected at a location, in respect to the UNF-MRD aperture, selected from a group consisting of: left, right, below, above and any combination thereof.

According to another embodiment of the present invention, wherein at least a portion of the RFSH comprises shielding selected from a group consisting of: magnetic shielding, RF shielding, physical shielding and any combination thereof.

According to another embodiment of the present invention, wherein the conduit is configured to shield the passage of frequencies selected from a group consisting of: 0-1000 MHz, 0-500 MHz, 0-200 MHz and any combination thereof.

According to another embodiment of the present invention, wherein the conduit is configured to shield electromagnetic interference by means selected from a group of: waveguide, RF filter, waveguide filter, attenuating material, and any combination thereof.

According to another embodiment of the present invention, wherein the RF interference is within a predetermined range.

According to another embodiment of the present invention, wherein the range is selected from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF shielding means reject frequencies in within a predetermined range.

The RF shielding means of claim 19, wherein the range is selected from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF-electromagnetic environment includes an item selected from a group consisting of RF welders, electronic article surveillance and RF identification devices, cordless phones, FM and AM broadcasting and receiving devices, and any combination thereof.

According to another embodiment of the present invention, wherein the RF interference is selected from a group consisting of continuous interference, transient interference, and any combination thereof.

According to another embodiment of the present invention, wherein the RII provided by the shielding is above a predetermined value.

According to another embodiment of the present invention, wherein the predetermined value is about 100 dB.

According to another embodiment of the present invention, wherein the magnetic field within a predetermined radius from the UNF-MRD is less than a predetermined value.

According to another embodiment of the present invention, wherein the predetermined radius is less than about 0.5 meter the predetermined value is less than about 20 mT.

20 mT is the weakest magnetism that may erase information from a credit card.

According to another embodiment of the present invention, wherein the RII provides no zipper effect in images produced by the UNF-MRD.

According to another embodiment of the present invention, wherein the UNF-MRD provides images with no Herringbone effect.

According to another embodiment of the present invention, wherein the UNF-MRD is compatible with ferromagnetic materials located further than a predetermined distance.

According to another embodiment of the present invention, wherein the predetermined distance is about 0.5 meters.

According to another embodiment of the present invention, a method for eliminating RF interference between a uniform non-fringing magnetic field resonance device (UNF-MRD) and an RF-electromagnetic environment surrounding the same, comprising steps of: (a) obtaining a UNF-MRD; and, (b) embedding RF shielding means; the RF shielding means provides radio interference immunity (RII) to the UNF-MRD from RF-electromagnetic environment; thereby, no RF and magnetic interference between the UNF-MRD and the RF-electromagnetic environment is generated.

According to another embodiment of the present invention, additionally comprising a step of providing the UNF-MRD with (a) a main longitudinal axis with a distal and proximal ends; (b) an open bore extended along the axis and terminated by an aperture located in the proximal end; and (c) a closure assembly which is shaped to fit the aperture.

According to another embodiment of the present invention, additionally comprising a step of selecting an RF shielding conduit (RFSC) for the RF shielding means, the RFSC having apertures shaped to permit passage of medical equipment tubing from the external environment of the UNF-MRD to inner space of the bore, affixed to the closure assembly, wherein the conduit is characterized by a length (l) and width (w), l:w ratio is greater than a predefined value n, thereby providing RF shielding.

According to another embodiment of the present invention, additionally comprising a step of connecting the RFSC in a non-protruding manner to the closure assembly, thereby providing indirect access between the bore and the external environment.

According to another embodiment of the present invention, additionally comprising a step of selecting the RFSC profile along the width is of a shape from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the present invention, additionally comprising a step of providing a wall along the length; the wall is of a shape selected from a group consisting of: straight, curved, polygonal, symmetrical, non-symmetrical and any combination thereof.

According to another embodiment of the present invention, additionally comprising a step of providing, to at least a portion of the RFSC, electromagnetic conductive material.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group consisting of: waveguide, RF filter, waveguide filter, attenuating material, and any combination thereof.

According to another embodiment of the present invention, additionally comprising a step of providing, to at least a portion of the RFSC, shielding selected from a group consisting of: magnetic shielding, RF shielding, physical shielding and any combination thereof.

According to another embodiment of the present invention, additionally comprising a step of affixing the RFSC to the closure assembly further comprising a hinge having at least one first connecting member connected to the UNF-MRD and at least one second connecting member, connected to the closure assembly, further wherein at least one first connecting member is maneuverably coupled to at least one second connecting member.

According to another embodiment of the present invention, additionally comprising a step of selecting an RF shielding hinge (RFSH) for the RF shielding means; the RFSH comprises at least one first connecting member connected to the UNF-MRD or the open bore thereof and at least one second connecting member, connected to the closure assembly; at least one first connecting member is maneuverably coupled to at least one second connecting member; the RFSH comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the present invention, additionally comprising a step of connecting the RFSH member to the UNF-MRD is connected at a location selected from a group consisting of: at least a portion of the UNF-MRD external wall, within at least a portion of the bore, at least a portion of the UNF-MRD aperture perimeter and any combination thereof.

According to another embodiment of the present invention, additionally comprising a step of connecting the hinge first connecting member at a location, in respect to the UNF-MRD aperture, selected from a group consisting of: left, right, below, above and any combination thereof.

According to another embodiment of the present invention, additionally comprising a step of selecting at least a portion of the RFSH comprises shielding from a group consisting of: magnetic shielding, RF shielding, physical shielding and any combination thereof.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group of: waveguide, RF filter, waveguide filter, attenuating material, and any combination thereof.

According to another embodiment of the present invention, additionally comprising a step of defining the RF interference within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, additionally comprising a step of rejecting the RF shielding means frequencies in within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF-electromagnetic environment includes an item selected from a group consisting of RF welders, electronic article surveillance and RF identification devices, cordless phones, FM and AM broadcasting and receiving devices, and any combination thereof.

According to another embodiment of the present invention, additionally comprising a step of selecting the RF interference from a group consisting of continuous interference, transient interference, and any combination thereof.

According to another embodiment of the present invention, wherein the RII provided by the shielding is above a predetermined value.

According to another embodiment of the present invention, wherein the predetermined value is about 100 dB.

According to another embodiment of the present invention, wherein the magnetic field within a predetermined radius from the UNF-MRD is less than a predetermined value.

According to another embodiment of the present invention, wherein the predetermined radius is less than about 0.5 meter the predetermined value is less than about 20 mT.

According to another embodiment of the present invention, additionally comprising a step of providing no zipper effect by the RII in images produced by the UNF-MRD.

According to another embodiment of the present invention, additionally comprising a step of providing by the UNF-MRD images with no Herringbone effect.

According to another embodiment of the present invention, wherein the UNF-MRD is compatible with ferromagnetic materials located further than a predetermined distance.

According to another embodiment of the present invention, wherein the predetermined distance is about 0.5 meters.

According to another embodiment of the present invention, wherein subjects going through an imaging process in the UNF-MRD are not obligated to be detached from medical equipment.

According to another embodiment of the present invention, additionally comprising a step of passing the medical equipment tubing through the conduit.

According to another embodiment of the present invention, a method for manufacturing a uniform non-fringing magnetic field resonance device (UNF-MRD) for imaging within an RF-electromagnetic environment surrounding the same, comprising steps of: (a) obtaining an UNF-MRD; and, (b) embedding RF shielding means; the RF shielding means provides radio interference immunity (RII) to the UNF-MRD from RF-electromagnetic environment; thereby, no RF and magnetic interference between the UNF-MRD and the RF-electromagnetic environment is generated.

According to another embodiment of the present invention, additionally comprising a step of providing the UNF-MRD with (a) a main longitudinal axis with a distal and proximal ends; (b) an open bore extended along the axis and terminated by an aperture located in the proximal end; and (c) a closure assembly which is shaped to fit the aperture.

According to another embodiment of the present invention, additionally comprising a step of selecting an RF shielding conduit (RFSC) for the RF shielding means, the RFSC having apertures shaped to permit passage of medical equipment tubing from the external environment of the UNF-MRD to inner space of the bore, affixed to the closure assembly, wherein the conduit is characterized by a length (l) and width (w), l:w ratio is greater than a predefined value n, thereby providing RF shielding.

According to another embodiment of the present invention, additionally comprising a step of connecting the RFSC in a non-protruding manner to the closure assembly, thereby providing indirect access between the bore and the external environment.

According to another embodiment of the present invention, additionally comprising a step of selecting the RFSC profile along the width is of a shape from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the present invention, additionally comprising a step of providing a wall along the length; the wall is of a shape selected from a group consisting of: straight, curved, polygonal, symmetrical, non symmetrical and any combination thereof.

According to another embodiment of the present invention, additionally comprising a step of providing, to at least a portion of the RFSC, electromagnetic conductive material.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group consisting of: waveguide, RF filter, waveguide filter, attenuating material, and any combination thereof.

According to another embodiment of the present invention, additionally comprising a step of providing, to at least a portion of the RFSC, shielding selected from a group consisting of: magnetic shielding, RF shielding, physical shielding and any combination thereof.

According to another embodiment of the present invention, additionally comprising a step of affixing the RFSC to the closure assembly further comprising a hinge having at least one first connecting member connected to the UNF-MRD and at least one second connecting member, connected to the closure assembly, further wherein at least one first connecting member is maneuverably coupled to at least one second connecting member.

According to another embodiment of the present invention, additionally comprising a step of selecting an RF shielding hinge (RFSH) for the RF shielding means; the RFSH comprises at least one first connecting member connected to the UNF-MRD or the open bore thereof and at least one second connecting member, connected to the closure assembly; at least one first connecting member is maneuverably coupled to at least one second connecting member; the RFSH comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the present invention, additionally comprising a step of connecting the RFSH member to the UNF-MRD is connected at a location selected from a group consisting of: at least a portion of the UNF-MRD external wall, within at least a portion of the bore, at least a portion of the UNF-MRD aperture perimeter and any combination thereof.

According to another embodiment of the present invention, additionally comprising a step of connecting the hinge first connecting member at a location, in respect to the UNF-MRD aperture, selected from a group consisting of: left, right, below, above and any combination thereof.

According to another embodiment of the present invention, additionally comprising a step of selecting at least a portion of the RFSH comprises shielding from a group consisting of: magnetic shielding, RF shielding, physical shielding and any combination thereof.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group of: waveguide, RF filter, waveguide filter, attenuating material, and any combination thereof.

According to another embodiment of the present invention, additionally comprising a step of defining the RF interference within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, additionally comprising a step of rejecting the RF shielding means frequencies in within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF-electromagnetic environment includes an item selected from a group consisting of RF welders, electronic article surveillance and RF identification devices, cordless phones, FM and AM broadcasting and receiving devices, and any combination thereof.

According to another embodiment of the present invention, additionally comprising a step of selecting the RF interference from a group consisting of continuous interference, transient interference, and any combination thereof.

According to another embodiment of the present invention, wherein the RII provided by the shielding is above a predetermined value.

According to another embodiment of the present invention, wherein the predetermined value is about 100 dB.

According to another embodiment of the present invention, wherein the magnetic field within a predetermined radius from the UNF-MRD is less than a predetermined value.

According to another embodiment of the present invention, wherein the predetermined radius is less than about 0.5 meter the predetermined value is less than about 20 mT.

According to another embodiment of the present invention, additionally comprising a step of providing no zipper effect by the RII in images produced by the UNF-MRD.

According to another embodiment of the present invention, additionally comprising a step of providing by the UNF-MRD images with no Herringbone effect.

According to another embodiment of the present invention, wherein the UNF-MRD is compatible with ferromagnetic materials located further than a predetermined distance.

According to another embodiment of the present invention, wherein the predetermined distance is about 0.5 meters.

According to another embodiment of the present invention, wherein subjects going through an imaging process in the UNF-MRD are not obligated to be detached from medical equipment.

According to another embodiment of the present invention, additionally comprising a step of passing the medical equipment tubing through the conduit.

According to another embodiment of the present invention, a standard of care (SOC) method for imaging a uniform non-fringing magnetic field resonance device (UNF-MRD) for imaging within an RF-electromagnetic environment surrounding the same, comprising steps of: (a) obtaining an UNF-MRD; and, (b) embedding RF shielding means; the RF shielding means provides radio interference immunity (RII) to the UNF-MRD from RF-electromagnetic environment; thereby, no RF and magnetic interference between the UNF-MRD and the RF-electromagnetic environment is generated.

According to another embodiment of the present invention, additionally comprising a step of providing the UNF-MRD with (a) a main longitudinal axis with a distal and proximal ends; (b) an open bore extended along the axis and terminated by an aperture located in the proximal end; and (c) a closure assembly which is shaped to fit the aperture.

According to another embodiment of the present invention, additionally comprising a step of selecting an RF shielding conduit (RFSC) for the RF shielding means, the RFSC having apertures shaped to permit passage of medical equipment tubing from the external environment of the UNF-MRD to inner space of the bore, affixed to the closure assembly, wherein the conduit is characterized by a length (l) and width (w), l:w ratio is greater than a predefined value n, thereby providing RF shielding.

According to another embodiment of the present invention, additionally comprising a step of connecting the RFSC in a non-protruding manner to the closure assembly, thereby providing indirect access between the bore and the external environment.

According to another embodiment of the present invention, additionally comprising a step of selecting the RFSC profile along the width is of a shape from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

According to another embodiment of the present invention, additionally comprising a step of providing a wall along the length; the wall is of a shape selected from a group consisting of: straight, curved, polygonal, symmetrical, non symmetrical and any combination thereof.

According to another embodiment of the present invention, additionally comprising a step of providing, to at least a portion of the RFSC, electromagnetic conductive material.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group consisting of: waveguide, RF filter, waveguide filter, attenuating material, and any combination thereof.

According to another embodiment of the present invention, additionally comprising a step of providing, to at least a portion of the RFSC, shielding selected from a group consisting of: magnetic shielding, RF shielding, physical shielding and any combination thereof.

According to another embodiment of the present invention, additionally comprising a step of affixing the RFSC to the closure assembly further comprising a hinge having at least one first connecting member connected to the UNF-MRD and at least one second connecting member, connected to the closure assembly, further wherein at least one first connecting member is maneuverably coupled to at least one second connecting member.

According to another embodiment of the present invention, additionally comprising a step of selecting an RF shielding hinge (RFSH) for the RF shielding means; the RFSH comprises at least one first connecting member connected to the UNF-MRD or the open bore thereof and at least one second connecting member, connected to the closure assembly; at least one first connecting member is maneuverably coupled to at least one second connecting member; the RFSH comprising a conduit, having apertures shaped to permit passage of medical equipment tubing from the external environment of the MRD to inner space of the bore, the conduit having a length (l) and width (w) is provided within at least a portion of the one first member, at least a portion of the one second member or in at least a portion of both members; l:w ratio is greater than a predefined value n, thereby RF shielding.

According to another embodiment of the present invention, additionally comprising a step of connecting the RFSH member to the UNF-MRD is connected at a location selected from a group consisting of: at least a portion of the UNF-MRD external wall, within at least a portion of the bore, at least a portion of the UNF-MRD aperture perimeter and any combination thereof.

According to another embodiment of the present invention, additionally comprising a step of connecting the hinge first connecting member at a location, in respect to the UNF-MRD aperture, selected from a group consisting of: left, right, below, above and any combination thereof.

According to another embodiment of the present invention, additionally comprising a step of selecting at least a portion of the RFSH comprises shielding from a group consisting of: magnetic shielding, RF shielding, physical shielding and any combination thereof.

According to another embodiment of the present invention, additionally comprising a step of configuring the conduit to shield the passage of frequencies selected from a group consisting of: 0 to about 1000 MHz, 0 to about 500 MHz, 0 to about 200 MHz and any combination thereof.

According to another embodiment of the present invention, additionally comprising a step of configuring the conduit to shield the electro-magnetic interference by means selected from a group of: waveguide, RF filter, waveguide filter, attenuating material, and any combination thereof.

According to another embodiment of the present invention, additionally comprising a step of defining the RF interference within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, additionally comprising a step of rejecting the RF shielding means frequencies in within a predetermined range.

According to another embodiment of the present invention, additionally comprising a step of selecting the range from a group consisting of: (a) from about 10 to about 100 MHz; (b) from about 0 to about 1000 MHz; (c) from about 0 to about 500 MHz; (d) from about 0 to about 200 MHz; and any combination thereof.

According to another embodiment of the present invention, wherein the RF-electromagnetic environment includes an item selected from a group consisting of RF welders, electronic article surveillance and RF identification devices, cordless phones, FM and AM broadcasting and receiving devices, and any combination thereof.

According to another embodiment of the present invention, additionally comprising a step of selecting the RF interference from a group consisting of continuous interference, transient interference, and any combination thereof.

According to another embodiment of the present invention, wherein the RII provided by the shielding is above a predetermined value.

According to another embodiment of the present invention, wherein the predetermined value is about 100 dB.

According to another embodiment of the present invention, wherein the magnetic field within a predetermined radius from the UNF-MRD is less than a predetermined value.

According to another embodiment of the present invention, wherein the predetermined radius is less than about 0.5 meter the predetermined value is less than about 20 mT.

According to another embodiment of the present invention, additionally comprising a step of providing no zipper effect by the RII in images produced by the UNF-MRD.

According to another embodiment of the present invention, additionally comprising a step of providing by the UNF-MRD images with no Herringbone effect.

According to another embodiment of the present invention, wherein the UNF-MRD is compatible with ferromagnetic materials located further than a predetermined distance.

According to another embodiment of the present invention, wherein the predetermined distance is about 0.5 meters.

According to another embodiment of the present invention, wherein subjects going through an imaging process in the UNF-MRD are not obligated to be detached from medical equipment.

According to another embodiment of the present invention, additionally comprising a step of passing the medical equipment tubing through the conduit.

Reference is now made to FIG. 1, which schematically illustrates the RF spectrum and its sources. It can be deduced from the table that an MRI device transmits in the range of about 10 to 100 MHz and therefore will mostly affect and be affected by other electronic device transmitting in the same range. Other electronic devices transmitting in this range are mainly RF welders (10 to 100 MHz), electronic article surveillance and RF identification (100 KHz to 5 GHz), cordless phones (1 MHz to 5 GHz), FM and AM broadcasting (100 KHz to 50 MHz and 50 to 100 MHz), respectively.

Figure 2:
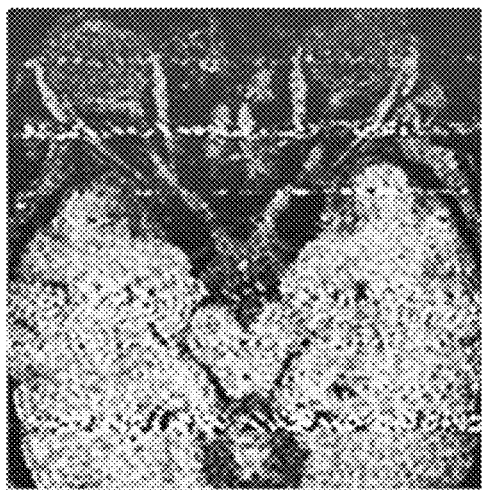
FIG. 2 shows the result of the zipper artifact on MRI imaging.

The result of RF interference on the function of an MRI device will be mostly on the imaging quality causing artifacts and noise. For example, the zipper effect, resulting from inhomogeneity of the magnetic field caused by interferences with radio frequency from various sources, appear as dashed lines as can be seen in FIG. 2.

The MRI's RF may also interfere with other electronic devices: it may disrupt radio broadcasting, it may reduce the sound quality of cordless phones (signal/noise ratio) and its reception range, it may disturb the function of RFID and electronic article surveillance by increasing their interference rejection.

The MRI magnet may affect ferromagnetic objects mainly by the missile effect in which ferromagnetic objects can be withdrawn into the MRI device in a very strong force. It may also cause a Torque effect on pacemakers that compromises their function and affect the homogeneity of other magnetic fields in its surrounding (for example, neighboring MRI devices.

The homogeneity of the MRI's magnet may be compromised by ferromagnetic objects in its surroundings, thus reducing the imaging quality of the device.

Reference is now made to FIG. 3 (200), which illustrates an MRI device (210) and its interactions with an RF transceiving device (220) (cordless phone in this example). FIG. 3A illustrates the interactions of an MRI comprising an infringing magnet and no RF shielding means and FIG. 3B illustrates an MRI device comprising a non-infringing magnet and RF shielding means (230). The RF shielding means may be either a waveguide or a Faraday cage.

The RF emitted from the cordless phone is indicated 230A and 230B in FIGS. 3A and 3B, respectively. In FIG. 3A, in which the MRI device is lacking shielding means, the RF emitted from the cordless phone (230A) is emitted within the MRI device, thus interfering the device's RF. In contrast, in an MRI device having RF shielding means (230) the RF emitted from the cordless phone (230B) does not enter the device and therefore does not affects its function. In a similar manner, the RF emitted from the MRI device (240) not having shielding means interferes with the cordless phone while in the MRI device having shielding means the MRI's RF remains trapped with the device. In addition, the MRI device in FIG. 3A has a fringing magnet that exerts stronger and broader magnetic field (250A) in comparison to an MRI comprising an infringing magnet the exerts a much weaker and narrower magnetic field (250B)

An MRI device having shielding means and infringing magnet makes it possible to carry out imaging process within an active RF environment. For example, it is possible to image with an MRI within an emergency room, which utilizes cordless phones and RFID tags for identifying patients. Utilizing this kind of MRI will enable receiving accurate imaging data without compromising the function of other electronic devices. It will also prevent hazardous consequences usually existing with an infringing magnet.

In a preferred embodiment of the invention, the RF shielding means comprising a U-shaped (e.g., U-shape, C-shape, W-shape etc.) conduit having an array of distal and proximal sealing walls, both are substantially perpendicular to the longitudinal axis and having upwards and downwards directions, and a recess in between the walls having length (upwards to downwards direction) and width (distal to proximal direction), wherein each of the proximal wall and the distal wall is having an aperture at opposite directions, and wherein in the recess, the ratio of length to width is greater than a predefined value n. The special structure of the conduit enables RF shielding whilst still keeping an opening for medical tubes to passage so a patient will not need to be detached from medical equipment he is connected to (respirator, intravenous feeding, etc.).

Figures 4A, 4B, 4C:
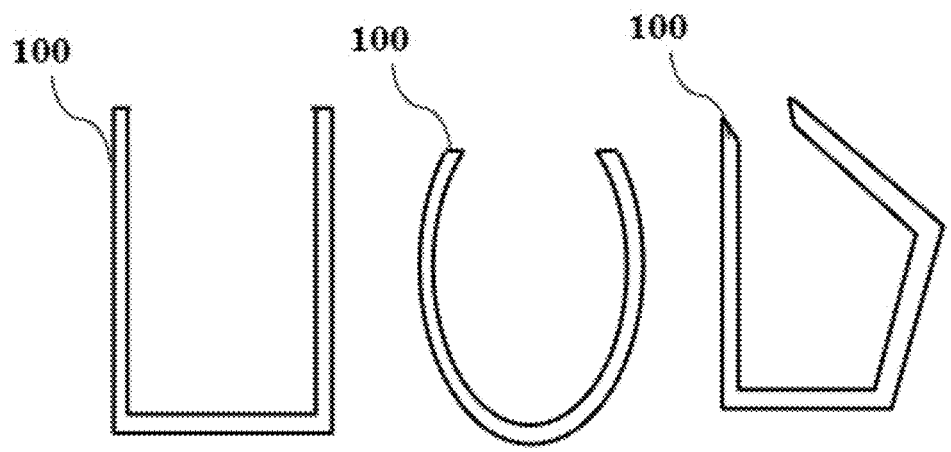
FIG. 4A is a schematic illustration of an embodiment of the U shaped conduit, in a side view profile.
FIG. 4B is a schematic illustration of an embodiment of the U shaped conduit, in a side view profile.
FIG. 4C is a schematic illustration of an embodiment of the U shaped conduit, in a side view profile.

Reference is now made to FIG. 4A schematically illustrating, in an out of scale manner, an embodiment of the invention. In this embodiment the U-shaped profile of the conduit (100) comprises walls connected in straight angles to one another.

Reference is now made to FIG. 4B schematically illustrating, in an out of scale manner, an embodiment of the invention. In this embodiment the U-shaped profile of the conduit (100) is a curved profile.

Reference is now made to FIG. 4C schematically illustrating, in an out of scale manner, an embodiment of the invention. In this embodiment the U-shaped profile of the conduit (100) is a non-symmetrical multifaceted shape profile.

Figures 4D, 4E, 4F:
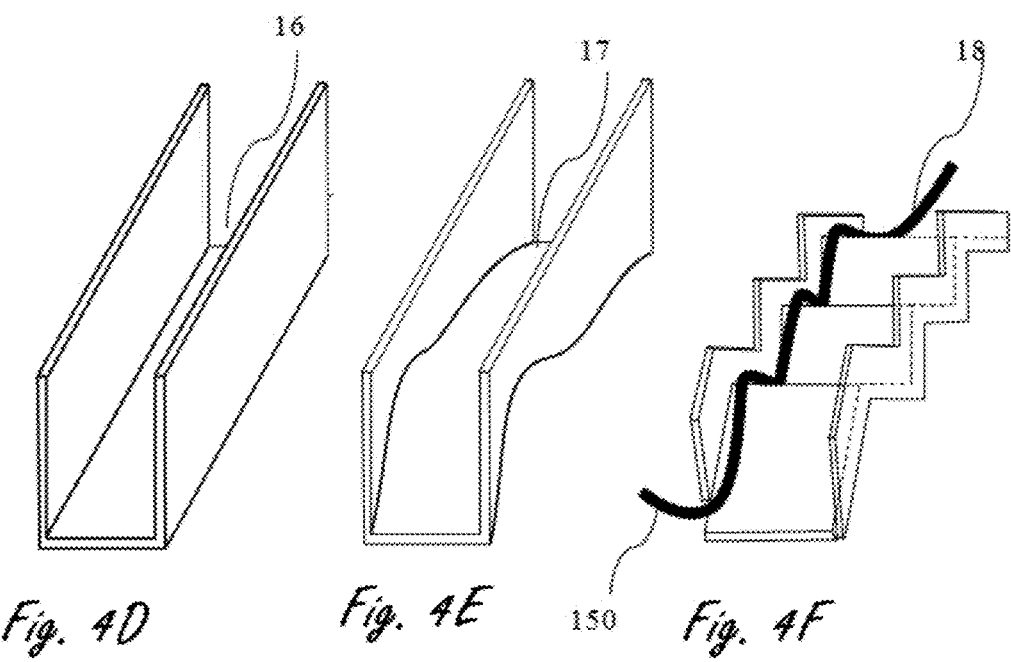
FIG. 4D is a schematic illustration of an embodiment of the U shaped conduit, in a perspective view, illustrating an embodiment of the longitudinal axis wall.
FIG. 4E is a schematic illustration of an embodiment of the U shaped conduit, in a perspective view, illustrating an embodiment of the longitudinal axis wall.
FIG. 4F is a schematic illustration of an embodiment of the U shaped conduit, in a perspective view, illustrating an embodiment of the longitudinal axis wall; and, FIG. 5 is a schematic illustration of test setup for evaluating the Immunity of Wrist II MRI to radiated disturbances at Cellular, Wi-Fi and RFID frequencies.

Reference is now made to FIG. 4D schematically illustrating, in an out of scale manner, an embodiment of the invention. In this embodiment the conduit wall (16) along its longitudinal axis is a straight planar surface.

Reference is now made to FIG. 4E schematically illustrating, in an out of scale manner, an embodiment of the invention. In this embodiment the conduit wall (17) along its longitudinal axis is a curved surface.

Reference is now made to FIG. 4F schematically illustrating, in an out of scale manner, an embodiment of the invention. In this embodiment the conduit wall (18) along its longitudinal axis is a multi-facet surface.

Example 1

Immunity to radiated disturbances at Cellular, Wi-Fi and RFID frequencies of a Wrist II MRI was tested by the Standards Institution of Israel. The Wrist II MRI is a uniform non-fringing magnetic field resonance device (UNF-MRD) comprising RF shielding means.

Figure 5:
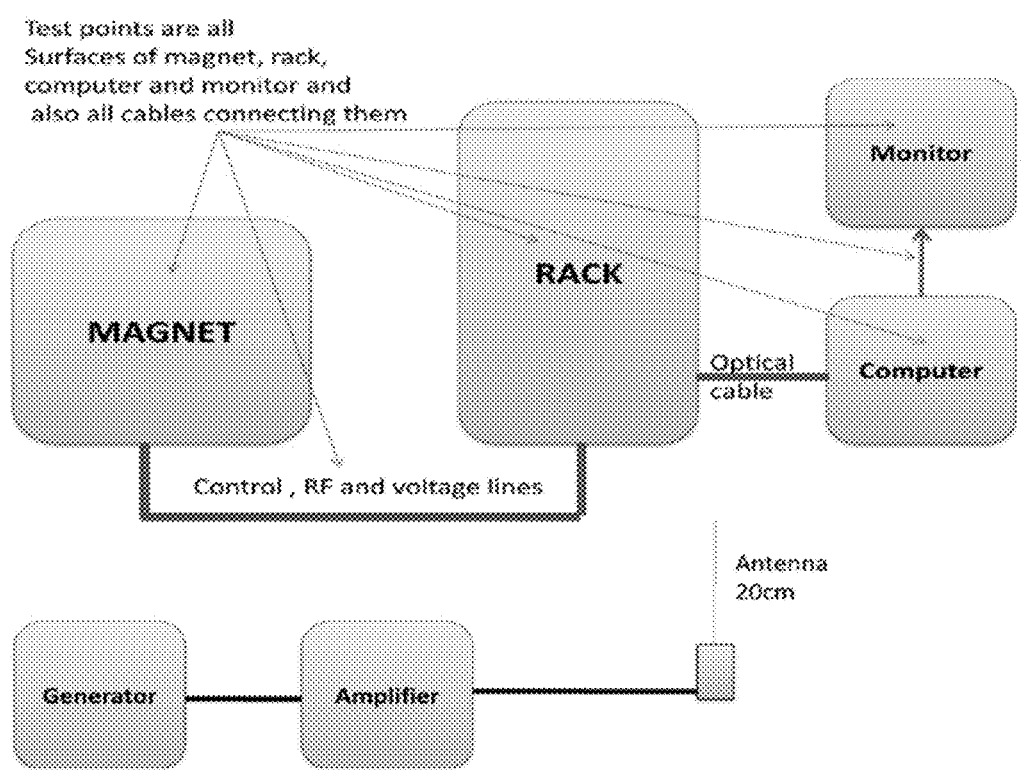

The objective of the test was to study the performance of the machine under cellular, Wi-Fi or RFID disturbance. The disturbance at frequencies representing Cellular, Wi-Fi and RFID was applied to all sides and interconnecting cables of equipment under test (EUT). The disturbance signal was transmitted by monopole antenna with 5 cm distance from EUT surface. The test setup can be viewed in FIG. 5.

The disturbance at frequencies representing Cellular, Wi-Fi and RFID was applied to all sides and interconnecting cables of EUT. The disturbance signal was transmitted by monopole antenna with 5 cm distance from EUT surface. Results can be viewed in Table 1:

TABLE 1

| Freq. (MHz) | Amplifier Forward power (W) | Type of Modulation | Magnet | Cables | Rack | Computer |
|---|---|---|---|---|---|---|
| 800-900 | 2 | PM, DC 50%, Rep rate 100 Hz | PASS | PASS | PASS | PASS |
| 1700-1900 | 2 | PM, DC 50%, Rep rate 100 Hz | PASS | PASS | PASS | PASS |
| 2400-2500 | 2 | PM, DC 50%, Rep rate 100 Hz | PASS | PASS | PASS | PASS |
| 13.56 | 2 | PM, DC 50%, Rep rate 100 Hz | PASS | PASS | PASS | PASS |

Performance criteria of the test: no change in performance of EUT is allowed during disturbance application; Program running at the EUT during the test: AMF 1.2.0.6; Running mode: MRI Scan. Conclusions of the test: no change in performance was observed during the test and therefore the Wrist II MRI is immune to RF radiation at least in the ranges tested.

What is claimed is:

1. In a uniform non-fringing magnetic field resonance device (UNF-MRD), an RF shielding means either embedded within or in connection with said UNF-MRD for providing said UNF-MRD a radio interference immunity (RII)

from RF-electromagnetic environment surrounding the same wherein said UNF-MRD is compatible with ferromagnetic materials located further than a predetermined distance of 0.5 meters.

2. The RF shielding means of claim 1, wherein said UNF-MRD is characterized by a main longitudinal axis with a distal and proximal ends and comprises (a) an open bore extended along said axis and terminated by an aperture located in said proximal end and (b), a closure assembly which is shaped to fit said aperture.

3. The RF shielding means of claim 2, wherein said RF shielding means comprises an RF shielding conduit (RFSC), having apertures shaped to permit passage of medical equipment tubing from the external environment of said UNF-MRD to inner space of said bore, affixed to said closure assembly, said conduit is characterized by a length (l) and width (w), l:w ratio is greater than a predefined value n, thereby providing RF shielding.

4. The RF shielding means of claim 3, wherein said RFSC is connected in a non-protruding manner to said closure assembly, thereby indirect access is provided between said bore and said external environment.

5. The RF shielding means of claim 3, wherein said RFSC profile along said width is of a shape selected from a group consisting of: curved U-shape, polygonal U-shape, C-shaped, V-shaped, W-shaped, symmetrical, non-symmetrical, cylinder, polygonal, straight faced, curved, closed shape, open shape and any combination thereof.

6. The RF shielding means of claim 3, wherein said RFSC comprises a wall along said length; said wall is of a shape selected from a group consisting of: straight, curved, polygonal, symmetrical, non symmetrical and any combination thereof.

7. The RF shielding means of claim 3, wherein at least a portion of said RFSC comprises electromagnetic conductive material.

8. The RF shielding means of claim 3, wherein said conduit is configured to shield the passage of frequencies selected from a group consisting of: 0 to about 1000 MHz, 0 to about 500 MHz, 0 to about 200 MHz and any combination thereof.

9. The RF shielding means of claim 3, wherein said conduit is configured to shield electro-magnetic interference by means selected from a group consisting of: waveguide, RF filter, waveguide filter, attenuating material, and any combination thereof.

10. The RF shielding means of claim 3, wherein at least a portion of said RFSC comprises shielding selected from a group consisting of: magnetic shielding, RF shielding, physical shielding and any combination thereof.

11. The RF shielding means of claim 3, wherein said RFSC is affixed to said closure assembly further comprising a hinge having at least one first connecting member connected to said UNF-MRD and at least one second connecting member, connected to said closure assembly, further wherein said at least one first connecting member is maneuverably coupled to said at least one second connecting member.

12. The RF shielding means of claim 2, wherein said RF shielding means comprises an RF shielding hinge (RFSH); said RFSH comprises at least one first connecting member connected to said UNF-MRD or said open bore thereof and at least one second connecting member, connected to said closure assembly; said at least one first connecting member is maneuverably coupled to said at least one second connecting member; said RFSH comprising a conduit, having apertures shaped to permit passage of medical equipment tubing from the external environment of said MRD to inner space of said bore, said conduit having a length (l) and width (w) is provided within at least a portion of said one first member, at least a portion of said one second member or in at least a portion of both members; l:w ratio is greater than a predefined value n, thereby RF shielding.

13. The RF shielding means of claim 12, wherein said RFSH member connected to said UNF-MRD is connected at a location selected from a group consisting of: at least a portion of said UNF-MRD external wall, within at least a portion of said bore, at least a portion of said UNF-MRD aperture perimeter and any combination thereof.

14. The RF shielding means of claim 12, wherein said hinge first connecting member is connected at a location, in respect to said UNF-MRD aperture, selected from a group consisting of: left, right, below, above and any combination thereof.

15. The RF shielding means of claim 12, wherein at least a portion of said RFSH comprises shielding selected from a group consisting of: magnetic shielding, RF shielding, physical shielding and any combination thereof.

16. The RF shielding means of claim 12, wherein said conduit is configured to shield the passage of frequencies selected from a group consisting of: 0-1000 MHz, 0-500 MHz, 0-200 MHz and any combination thereof.

17. The RF shielding means of claim 12, wherein said conduit is configured to shield electro-magnetic interference by means selected from a group of: waveguide, RF filter, waveguide filter, attenuating material, and any combination thereof.

18. The RF shielding means of claim 1, wherein said RF interference is within a predetermined range.

19. The RF shielding means of claim 18, wherein said range is selected from a group consisting of: (a) from about 10 to about 100 MHz; (b) from about 0 to about 1000 MHz; (c) from about 0 to about 500 MHz; (d) from about 0 to about 200 MHz; and any combination thereof.

20. The RF shielding means of claim 1, wherein said RF shielding means reject frequencies in within a predetermined range.

21. The RF shielding means of claim 20, wherein said range is selected from a group consisting of: (a) from about 10 to about 100 MHz; (b) from about 0 to about 1000 MHz; (c) from about 0 to about 500 MHz; (d) from about 0 to about 200 MHz; and any combination thereof.

22. The RF shielding means of claim 1, wherein said RF-electromagnetic environment includes an item selected from a group consisting of RF welders, electronic article surveillance and RF identification devices, cordless phones, FM and AM broadcasting and receiving devices, and any combination thereof.

23. The RF shielding means of claim 1, wherein said RF interference is selected from a group consisting of continuous interference, transient interference, and any combination thereof.

24. The RF shielding means of claim 1, wherein said RII provided by said shielding is above a predetermined value.

25. The RF shielding means of claim 24, wherein said predetermined value is about 100 dB.

26. The RF shielding means of claim 1, wherein the magnetic field within a predetermined radius from said UNF-MRD is less than a predetermined value.

27. The RF shielding means of claim 26, wherein said predetermined radius is less than about 0.5 and said predetermined value is less than about 20 mT.

28. The RF shielding means of claim 1, wherein said RII provides no zipper effect in images produced by said UNF-MRD.

29. The RF shielding means of claim 1, wherein said UNF-MRD provides images with no Herringbone effect.

\* \* \* \* \*